US005506101A

United States Patent [19]
Fischel-Ghodsian et al.

[11] Patent Number: 5,506,101
[45] Date of Patent: Apr. 9, 1996

[54] METHOD FOR DETECTION OF SUSCEPTIBILITY MUTATIONS FOR OTOTOXIC DEAFNESS

[75] Inventors: Nathan Fischel-Ghodsian, Los Angeles; Toni R. Prezant, Reseda, both of Calif.

[73] Assignee: Cedars-Sinai Medical Center, Los Angeles, Calif.

[21] Appl. No.: 85,996

[22] Filed: Jun. 30, 1993

[51] Int. Cl.⁶ ............................. C12Q 1/68; C12P 19/34; C07H 21/04

[52] U.S. Cl. ......................... 435/6; 435/91.2; 536/24.31; 935/77; 935/78

[58] Field of Search ................ 435/6, 91.2; 536/24.31; 935/77, 78

[56] References Cited

PUBLICATIONS

Prezant et al. (1992) American J. Medical Genetics 44:465–472.
Higashi et al. (1989) Clin. Genet. 35:433–436.
Hu et al. (1991) J. Med. Genet. 28:79–83.
Bu, X et al. (1993) Genet. Epidem. 10(1):3–15.
Moazed et al. (1987) Nature 327:389–394.

*Primary Examiner*—W. Gary Jones
*Assistant Examiner*—Lisa Arthur
*Attorney, Agent, or Firm*—Jeffer, Mangels, Butler & Marmaro

[57] ABSTRACT

Method for detection of mitochondrial nucleotide associated with predisposition for ototoxic deafness, especially deafness associated with the administration of aminoglycosides, is described.

19 Claims, 3 Drawing Sheets

3' END OF HUMAN MITOCHONDRIAL 12S rRNA

3' END OF E. COLI 16S rRNA

Fig. 2B

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear     ( i i ) MOLECULE TYPE: DNA (genomic)

( i x ) FEATURE:
        ( A ) NAME/KEY: CDS
        ( B ) LOCATION: 1..15

( x i ) SEQUENCE DESCRIPTION: SEQ ID NO:1:

CGACTTGTCT CCTCT 15

( 2 ) INFORMATION FOR SEQ ID NO:2:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear     ( i i ) MOLECULE TYPE: DNA (genomic)

( i x ) FEATURE:
        ( A ) NAME/KEY: CDS
        ( B ) LOCATION: 1..15

( x i ) SEQUENCE DESCRIPTION: SEQ ID NO:2:

CGACTTGCCT CCTCT 15

( 2 ) INFORMATION FOR SEQ ID NO:3:

( i ) SEQUENCE CHARACTERISTICS:
    ( A ) LENGTH: 127 base pairs
    ( B ) TYPE: nucleic acid
    ( C ) STRANDEDNESS: single
    ( D ) TOPOLOGY: linear ( i i ) MOLECULE TYPE: rRNA ( i x ) FEATURE:
    ( A ) NAME/KEY: misc_RNA
    ( B ) LOCATION: 1..127

( x i ) SEQUENCE DESCRIPTION: SEQ ID NO:3:

```
AUGCACACCG  CCCGUCACCC  UCCUCAAGUA  UACUUCAAAG  GACAUUUAAC  UAAAACCCCU      60

ACGCAUUUAU  AUAGAGGAGA  RCAAGUCGUA  ACAUGGUAAG  UGUACUGGAA  AGUGCACUUG     120

GACGAAC                                                                    127
```

( 2 ) INFORMATION FOR SEQ ID NO:4:

( i ) SEQUENCE CHARACTERISTICS:
    ( A ) LENGTH: 151 base pairs
    ( B ) TYPE: nucleic acid
    ( C ) STRANDEDNESS: single
    ( D ) TOPOLOGY: linear ( i i ) MOLECULE TYPE: rRNA ( i x ) FEATURE:
    ( A ) NAME/KEY: misc_RNA
    ( B ) LOCATION: 1..151

( x i ) SEQUENCE DESCRIPTION: SEQ ID NO:4:

```
AUGCACACCG  CCCGUCACAC  CAUGGGAGUG  GGUUGCAAAA  GAAGUAGGUA  GCUUAACCUU      60

CGGGAGGGCG  CUUACCACUU  UGUGAUUCAU  GACUGGGGUG  AAGUCGUAAC  AAGGUAACCG     120

UAGGGGAACC  UGCGGUUGGA  UCACCUCCUU  A                                     151
```

METHOD FOR DETECTION OF SUSCEPTIBILITY MUTATIONS FOR OTOTOXIC DEAFNESS

This invention was made with Government support under Grant No. DC 01402 awarded by the National Institutes of Health/NIDCD. The Government has certain rights in this invention.

BACKGROUND OF THE INVENTION

1. Field of the Invention

This invention relates to the area of genetic diagnosis. More specifically, the invention relates to detection of an alteration of wild-type mitochondrial ribosomal RNA(rRNA) which is associated with ototoxic deafness in humans.

2. Description of Related Art

Sensorineural deafness, either in conjunction with neuromuscular diseases or with diabetes, has been associated with heteroplasmic mitochondrial DNA (mtDNA) mutations (Shoffner, et al., *Adv. Human Genet.*, 19:267–330, 1990; Ballinger, et al., *Nature Genet.*, 1:11–15, 1992; van den Ouweland, et al., *Nature Genet.*, 1:368–371, 1992; Reardon, et al., *Lancet*, 34:1376–1379, 1992). The likelihood of mtDNA mutations has also been suggested in two forms of non-syndromic deafness. A maternal inheritance pattern has been reported in several pedigrees in the Far East with familial aminoglycoside-induced deafness (Higashi, *Clin. Genet.*, 35:433–436, 1989; Hu, et al., *J. Med. Genet.*, 28:79–83, 1991), and a single large Arab-Israeli pedigree with maternally-inherited congenital deafness has been described (Jaber, et al., *J. Med. Genet.*, 29:86–90, 1992).

Mitochondrial DNA is transmitted exclusively through mothers, since the sperm apparently contributes no mitochondria to the zygote. This leads to the expectation that a defect in a mitochondrial gene should lead to disease equally in both sexes, but can only be transmitted through the maternal line. There are hundreds of mitochondria in each cell and they serve a variety of metabolic functions, the most important being the synthesis of ATP by oxidative phosphorylation. Each mitochondrion contains several mitochondrial DNA (mtDNA) chromosomes, which in humans are 16,569 basepairs (bp) double-stranded circles. Replication, transcription, and translation of the mtDNA occurs within the mitochondrion. The mitochondrial DNA encodes 13 messenger RNAs, and the large and small ribosomal RNAs and 22 transfer RNAs which are necessary for their translation. The messenger RNAs are translated on mitochondrion-specific ribosomes, using a mitochondrion-specific genetic code, into 13 proteins. These proteins interact with approximately sixty nuclear encoded proteins to form the five enzyme complexes required for oxidative phosphorylation.

Irreversible hearing loss is the main complication of aminoglycoside antibiotics such as streptomycin, gentamicin, and kanamycin (Sande, et al., Antimicrobial agents, in: Goodman and Gilman's *The Pharmacological Basis of Therapeutics*, 8th edition. eds, Gilman, et al., Pergamon Press, Inc., Elmsford, N.Y., pp 1098–1116, 1990). In China, due to widespread use of aminoglycosides, nearly 25% of all deaf-mutes in one district of Shanghai could trace the cause of hearing loss to aminoglycoside usage (Hu, et al., *J. Med. Genet.*, 28:79–93, 1991). Of these patients, roughly ¼ had other relatives with ototoxic deafness. In all of the 22 cases in which vertical transmission of this susceptibility could be traced, the inheritance pattern matched that of a mitochondrially-inherited trait, i.e., being transmitted only through females. A similar situation occurred in Japan, where Higashi tabulated 28 families with streptomycin-induced deafness, and found that in all but two cases, the susceptibility trait was maternally-inherited (Higashi, *Clin. Genet.*, 35:433–436, 1989). Hu, et al., supra also noted that the majority of familial cases received antibiotics for a much shorter period than the sporadic cases, implying the presence of a predisposing mutation or genetic susceptibility (Hu, et al., supra).

The mitochondrial ribosome in the cochlea is the most likely target of aminoglycoside ototoxicity, since the "natural target" of aminoglycosides is the evolutionarily-related bacterial ribosome (Sande, et al., supra). In bacterial studies, aminoglycosides appear to stabilize mismatched aminoacyl-tRNAs in the 70S ribosome, allowing misreading of the mRNA during translation (Hornig, et al., *Biochimie*, 69:803–813, 1987). In addition to their interactions with ribosomal proteins, aminoglycosides bind to the *E. coli* 16S rRNA, as demonstrated by chemical protection and crosslinking experiments (Moazed, et al., *Nature*, 327:389–394, 1987; Gravel, et al., *Biochemistry*, 26:6227–6232, 1987). These physical experiments predict regions of the small rRNA which are important in translational fidelity. Their relevance has been borne out by the isolation of aminoglycoside-resistance mutations in bacteria, yeast mitochondria, Tetrahymena, and chloroplasts which map to the predicted regions of the evolutionarily conserved small rRNA (Tzagaloff, et al., *J. Biol. Chem.*, 257:5921–5928, 1982; Spangler, et al., *J. Biol. Chem.*, 260: 6334–6340, 1985; Gauthier, et al., *Mol. Gen. Genet.*, 214:192–197, 1988; Melancon, et al., *Nucl. Acids Res.*, 16:9631–9639, 1988). Thus, the mitochondrial rRNA genes, and especially the corresponding 12S rRNA gene, become prime candidates for the site of the mtDNA mutation in maternally-inherited aminoglycoside-induced deafness.

Although the role of the mitochondrial DNA in ototoxic deafness has been suspected, no adequate diagnostic test was available to identify those individuals at risk. Consequently, at least where the ototoxin is an aminoglycoside antibiotic, physicians have been faced with the dilemma of choosing between the use of the antibiotic and the potential irreversible loss of hearing which might occur in the patient. The present invention addresses this problem by providing a rapid, non-invasive, and highly accurate diagnostic test which can identify individuals at risk for ototoxic deafness.

SUMMARY OF THE INVENTION

The present invention arose from the seminal discovery that nucleic acid having an altered nucleotide sequence is present in the mitochondria of individuals predisposed to ototoxic deafness.

As a consequence of this discovery, the invention for the first time allows individuals predisposed to ototoxic deafness to be screened before exposure to an ototoxin, such as an antibiotic, using techniques which are non-invasive, rapid, and sensitive.

BRIEF DESCRIPTION OF THE DRAWINGS

FIG. 1 represents three pedigrees with maternally-transmitted aminoglycoside-induced deafness. Solid symbols indicate individuals treated with streptomycin before high frequency sensorineural hearing loss ensued; the father of proband A (hatched symbol) was deaf from unknown causes. Horizontal bars indicate individuals whose DNA was sampled. Probands are indicated by arrows. Pedigrees A and C originally are from Shanghai. Pedigree B is from Beijing.

FIG. 2 is the 3' end of human mitochondrial 12S rRNA (2A) and the corresponding region of E. coli 16S rRNA (2B) (SEQ. I.D. NOS.3 and 4, respectively), showing the site of the 1555 A to G mutation in the four pedigrees with maternally-transmitted deafness. The functional regions of the E. coli 16S rRNA are depicted as follows: the sequence in { } is crosslinked to streptomycin; *, nucleotides that bind tRNA; ●, nucleotides at the ribosomal subunit interface; nucleotides in bold, altered activity to chemical modification upon aminoglycoside binding; underlined nucleotides in the E. coli sequence, sites of aminoglycoside resistance mutations in other species.

DETAILED DESCRIPTION OF THE INVENTION

The present invention relates to a method of detecting a nucleic acid having an altered nucleotide sequence, wherein the presence of the altered nucleic acid sequence is associated with a predisposition to ototoxic deafness. The altered nucleotide sequence, or the corresponding region of the nucleotide sequence of a normal individual not susceptible to ototoxic deafness, is referred to as the "target nucleic acid sequence". The target nucleotide sequence may be, for example, a mutant nucleotide, a restriction fragment length polymorphism (RFLP), a deletion, insertion, or rearrangement, a nucleotide substitution, or any other mammalian nucleic acid sequence of interest which is associated with an increased susceptibility, or predisposition for ototoxic deafness.

The present invention is based on the fundamental discovery that mutational events associated with ototoxic deafness occur in the mitochondrial gene which encodes mitochondrial rRNA. Although it is previously suspected that mitochondrial gene(s) were related in some way to ototoxic deafness, it was not known that a target gene of these deletions was the rRNA gene.

According to the method of the present invention, alteration of the wild-type gene is detected. "Alteration of a wild-type gene" according to the present invention encompasses all forms of mutations—including deletions. The alteration may be due to either rearrangements such as insertions, inversions, and deletions, or to point mutations. Deletions may be of the entire mitochondrial rRNA gene or only a portion of the gene. The findings of mutations thus provides evidence of a possible predisposition to ototoxic deafness. A mitochondrial rRNA allele which is not deleted can be screened for other mutations, such as insertions, small deletions, and point mutations. It is believed that mutations found in the mitochondrial rRNA and gene produce a predisposition for ototoxic deafness by "tightening" the binding pocket for the toxin on the mutant rRNA as compared to wild-type (non-susceptible) rRNA. This is particularly true where the ototoxin is an aminoglycoside. In this latter case, it is believed that the mutation results in a secondary structure for the mitochondrial rRNA which resembles a bacterial rRNA and, thereby, increases the susceptibility of the mitochondrial rRNA to bacterial antibiotics which act at the level of the bacterial ribosome. Additional candidate genes for susceptibility mutations are the nuclear encoded mitochondrial ribosomal protein genes, genes related to ototoxin uptake or transport, and genes involved in ototoxin metabolism.

Detection of point mutations may be accomplished by molecular cloning of the allele (or alleles) present in the specimen and sequencing that allele(s) using techniques well known in the art. Alternatively, the polymerase chain reaction (PCR) can be used to amplify gene sequences directly from a mitochondrial DNA preparation from the specimen. The DNA sequence of the amplified sequences can then be determined. Alternatively, single-stranded conformational polymorphism (SSCP), heteroduplex, and chemical cleavage methods can be used to pinpoint the location of mutation(s), prior to sequencing.

The polymerase chain reaction itself is well known in the art (Saiki, et al., *Science*, 239:487, 1988; U.S. Pat. Nos. 4,683,203 and 4,683,195). Specific primers which can be used in order to amplify the target nucleotide sequence will be discussed in more detail below. Normal and mutant oligonucleotides can be used to detect the target sequence by hybridizing to the PCR-amplified product, in a technique known as allele-specific oligonucleotide (ASO) hybridization. The ligase chain reaction, which is known in the art, can also be used to amplify mitochondrial sequences (Wu, et al., *Genomics*, 4:560, 1989). In addition, a technique known as allele-specific PCR can be used (Ruano and Kidd, *Nucleotic Acids Research*, 17:8392, 1989). According to this technique, primers are used which hybridize at their 3' ends to a particular mitochondrial rRNA mutation. If the particular mutation is not present, an amplification product is not observed. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Other techniques for detecting insertions and deletions as are known in the art can be used.

When it is desired to amplify the target nucleotide sequence before detection, this can be accomplished using oligonucleotide(s) which are primers for amplification. These unique oligonucleotide primers are based upon identification of the flanking regions contiguous with the mutant nucleotide sequence. For example, in the case of a 12S rRNA mutant specifically disclosed herein, these oligonucleotide primers comprise sequences which are capable of hybridizing with the flanking nucleotide sequences at nt 530–549 in the heavy strand and nt 1899–1880 in the light strand, based on the consensus mitochondrial sequence, and sequences complementary thereto.

As described herein, the mtDNA sequence in two different disorders with a maternally-transmitted susceptibility to non-syndromic deafness, one requiring an extrinsic agent and the other requiring a postulated nuclear mutation for phenotypic expression, were analyzed. A mtDNA mutation at nt 1555 in the 12S rRNA gene was identified, that appears to be the pathogenic mutation for the following reasons: (1) it was the only mutation common to all four families, (2) it was not present in 278 normal hearing controls, most of whom are ethnically matched, (3) no other rare mutation was found in the candidate genes of the three families with aminoglycoside-induced deafness, (4) none of the other rare mutations identified in the Arab-Israeli family has been ascribed a pathologic role in any mitochondrial disorder or was found in the families with ototoxic deafness, (5) it changes a nucleotide in a highly conserved region of the 12S rRNA, and (6) the mutated nucleotide in the 12S rRNA gene is in the region known to bind aminoglycosides (Moazed, et al., supra), and in which aminoglycoside-resistance mutations have been found in other species (Tzagaloff, et al., supra., Spangler, et al., supra).

The 1555 A→G mutation was the only one of the three sequence changes identified in the families with ototoxic deafness which showed a unique correlation with the disease. The two other mutations, 663 A→G and 1736 A→G, were also found in all three pedigrees with maternally-inherited ototoxic deafness, but both of these mutations are common Chinese polymorphisms, with a frequency of 10–11%. Since both of these mutations occurred together in 13 control individuals, the nt 1555 mutation most likely arose on a mitochondrial chromosome having these two mutations. It may not be that the 663 A→G and 1736 A→G by themselves are causative mutations, because the overall incidence of aminocyside ototoxic deafness is estimated at 1:10,000 (Hu, et al., supra). More importantly, at least four of the control individuals with both of these mutations received streptomycin, with no ill effects.

Several family-specific mutations in the Arab-Israeli pedigree were found, which could contribute to the disease phenotype, or enhance the effect of the 1555 A→G mutation. By analogy to Leber's hereditary optic neuroretinopathy (LHON), a nerve-specific mitochondrial disorder which might also require the involvement of an additional nuclear gene (Vikki, et al., *Am. J. Hum. Genet.*, 48:486–491, 1991; Bu, et al., *Proc. Natl. Acad. Sci. USA*, 88:8198–8202, 1991), any or all of these rare mutations may interact to produce a "pathogenic haplotype". The majority of LHON patients have single mtDNA point mutations (Wallace, et al., *Science*, 242:1427–1430, 1988; Howell, et al., *Am. J. Hu. Genet.*, 49:929–950, 1991; Howell, et al., *Am. J. Hum. Genet.*, 48:935–942, 1991; Huoponen, et al., *Am. J. Hum. Genet.*, 48:1147–1153, 1991), but some LHON cases appear to be due to a multiplicity of mutations, with their combinatorial effect resulting in disease (Brown, et al., *Genetics*, 130:163–173, 1992; Johns, et al., *Biochem. Biophys. Res. Commun.*, 174:1324–1330, 1991; Brown, et al., *Am. J. Hum. Genet.*, 51:378–385, 1992). Because the 1555 mutation was found in three other pedigrees with maternally-transmitted susceptibility to deafness, this mutation is believed to be the causative defect in the Arab-Israeli pedigree. Possibly the additional mtDNA mutations in this family participate to impair oxidative phosphorylation below a threshold required in the developing cochlea. All of the family members tested had the pathogenic haplotype, with each mutation appearing homoplasmic (heteroplasmy, if present, would have been at levels (10% in blood). Therefore, the reason that unaffected family members with the identical mtDNA sequence are not deaf is presumably due to the absence of homozygosity for the putative autosomal recessive mutation.

While not wanting to be bound to a particular theory, it is believed that a two-hit model can explain the development of non-syndromic deafness in these pedigrees. In addition to the underlying 1555 A→G mutation, the disease can be precipitated by the exogenous administration of aminoglycosides, which accumulate in the cochlea (Sande, et al., supra), or, in the Arab-Israeli pedigree, by the interaction of a hypothetical cochlear-specific ribosomal subunit with the 12S rRNA mutation. Either event would disturb or abolish the translational ability of the mitochondrial ribosome.

Figure 2A:
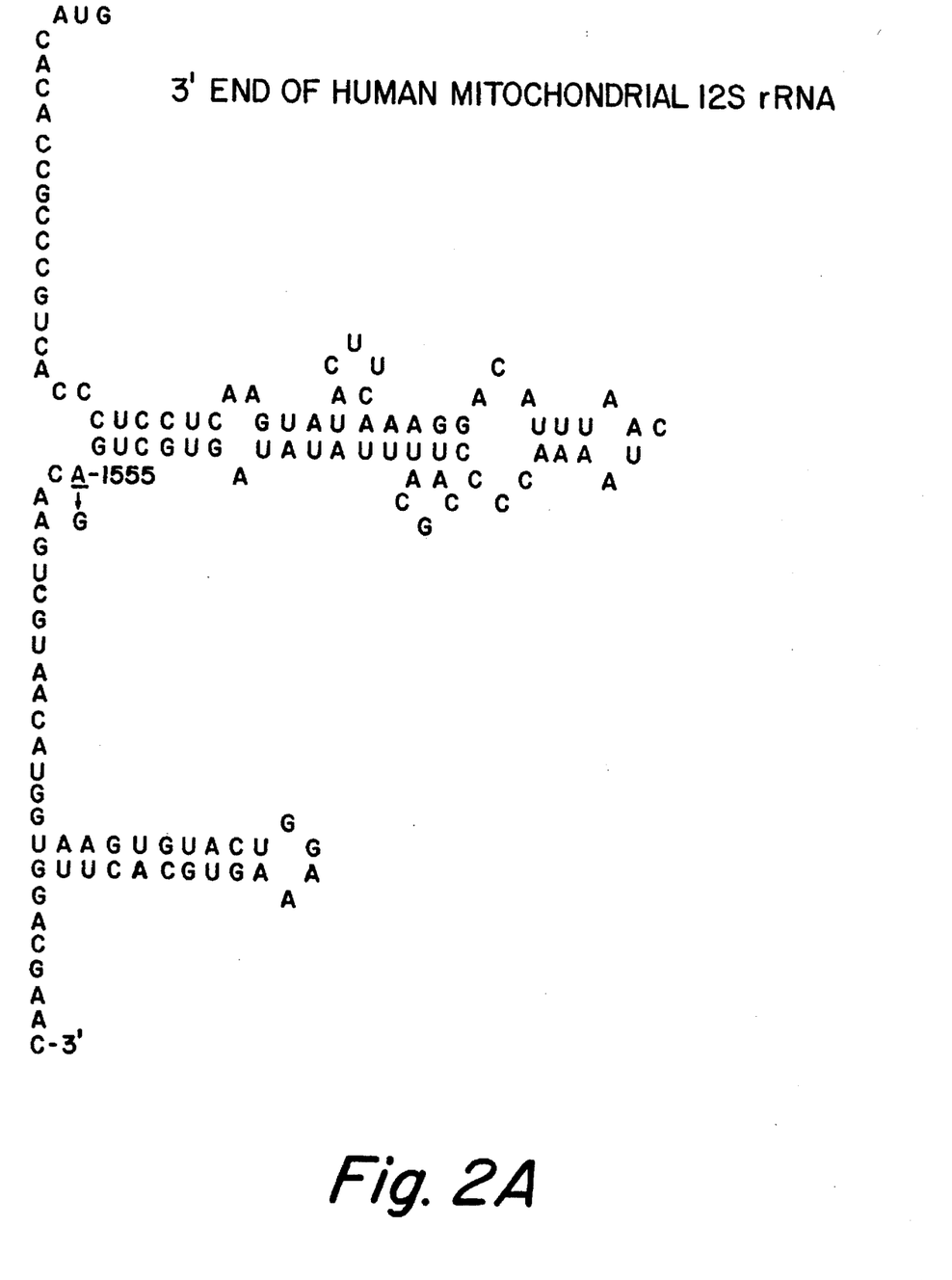
Figure 2B:
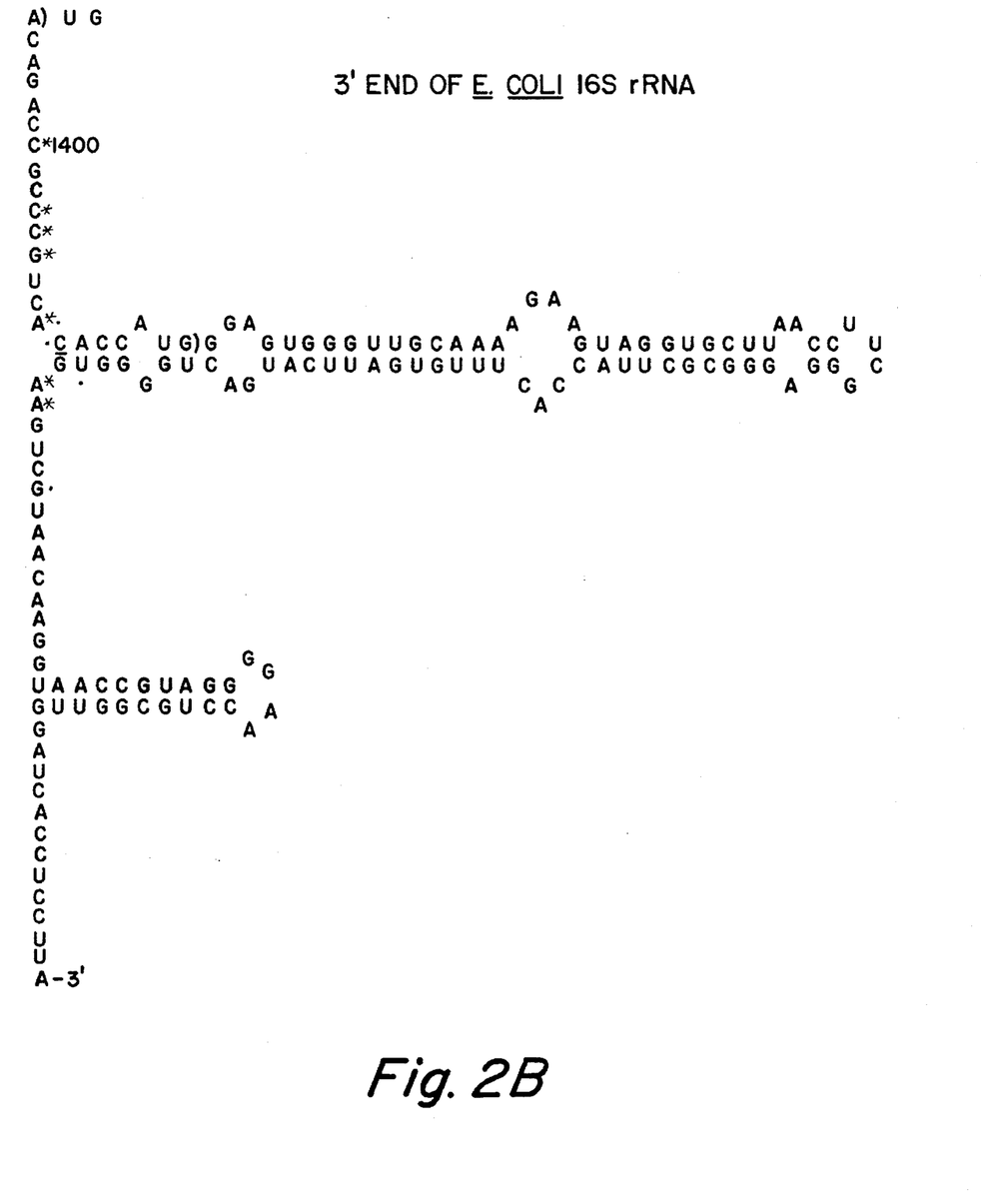

The 1555 A→G mutation affects a highly conserved domain of the small rRNA (FIG. 2), which has two single-stranded regions with conserved sequence, separated by two structurally conserved stem-loops in organisms as diverse as bacteria, plants, invertebrates, and mammals (Neefs, et al., supra; Gutell, et al., supra; Noller, et al., *Ann. Rev. Biochem.*, 53:119–162, 1984). Bacterial studies have shown that this portion of the molecule is part of the aminoacyl site, in which mRNAs are decoded, and lies at the ribosomal subunit interface (Hornig, et al., supra; Moazed, et al., supra; Brimacombe, *Biochemistry*, 27:4207–4213, 1988). Aminoglycosides affect translational fidelity by binding to this decoding region and stabilizing mismatched aminoacyl tRNAs (Hornig, et al., supra). Several nucleotides in this region (indicated in bold in FIG. 2) are implicated in aminoglycoside binding, since they have altered reactivity to chemical modifying agents when streptomycin, gentamicin, neomycin, kanamycin, or hygromycin are bound (Gravel, et al., supra). Streptomycin also crosslinks this region to another part of the *E. coli* small rRNA (Gravel, et al., supra), in which streptomycin resistance mutations are found (Montandon, et al., *EMBO J.*, 5: 3705–3708, 1986; Etzold, et al., *FEBS Lett.*, 219: 343–346, 1987).

Lastly, this region is important in aminoglycoside function, because aminoglycoside-resistance mutations (underlined in FIG. 1) were found in the analogous sites of small rRNAs in yeast mitochondria (Tzagaloff, et al., supra) and Tetrahymena (Spangler, et al., supra). Significantly, two of these mutations break the basepair which is adjacent to our mutation site, in effect "widening" the aminoglycoside-binding pocket. In contrast, the 1555 A→G mutation can produce a new C-G basepair, elongating the stem/loop and "tightening" this area, making the secondary structure resemble more closely that of the bacterial small rRNA. In is believed that the 1555 A→G mutation lengthens this helix, resulting in greater aminoglycoside binding and increased susceptibility to the effects of these antibiotics on translational fidelity.

The primers which can be used according to the method of the invention embrace oligonucleotides of sufficient length and appropriate sequence so as to provide specific initiation of polymerization of a significant number of nucleic acid molecules containing the target nucleic acid. In this manner, it is possible to selectively amplify the specific target nucleic acid sequence containing the nucleic acid of interest. Specifically, the term "primer" as used herein refers to a sequence comprising two or more deoxyribonucleotides or ribonucleotides, preferably at least eight, which sequence is capable of initiating synthesis of a primer extension product, which is substantially complementary to a target nucleic acid strand. The oligonucleotide primer typically contains 15–22 or more nucleotides, although it may contain fewer nucleotides.

Experimental conditions conducive to synthesis include the presence of deoxynucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent for polymerization. The exact length of primer will depend on many factors, including temperature, buffer, and nucleotide composition.

Primers used according to the method of the invention are designed to be substantially complementary to each strand of mutant or wild-type nucleotide sequence to be amplified. "Substantially complementary" means that the primers must be sufficiently complementary to hybridize with their respective strands under conditions which allow the agent for polymerization to function. In other words, the primers should have sufficient complementarity with the flanking sequences to hybridize therewith and permit amplification of the target nucleotide sequence. Preferably, the terminus of the primer that is extended has perfectly base paired complementarity with the complementary target sequence.

Oligonucleotide primers used according to the invention are employed in any amplification process that produces increased quantities of target nucleic acid. Typically, one primer is complementary to the negative (−) strand of the target nucleotide sequence and the other is complementary to the positive (+) strand. Annealing the primers to denatured nucleic acid followed by extension with an enzyme, such as the large fragment of DNA Polymerase I (Klenow) or Taq DNA polymerase and nucleotides or ligases, results in newly synthesized + and − strands containing the target nucleic acid. Because these newly synthesized nucleic acids are also templates, repeated cycles of denaturing, primer annealing, and extension results in exponential production of the region (i.e., the target nucleotide sequence) defined by the primer. The product of the amplification reaction is a discrete nucleic acid duplex with termini corresponding to the ends of the specific primers employed. Those of skill in the art will know of other amplification methodologies which can also be utilized to increase the copy number of target nucleic acid.

The oligonucleotide primers for use in the invention may be prepared using any suitable method, such as conventional phosphotriester and phosphodiester methods or automated embodiments thereof. In one such automated embodiment, diethylphosphoramidites are used as starting materials and may be synthesized as described by Beaucage, et al. (*Tetrahedron Letters*, 22:1859–1862, 1981). One method for synthesizing oligonucleotides on a modified solid support is described in U.S. Pat. No. 4,458,066. As noted above, one method of amplification which can be used according to this invention is the polymerase chain reaction (PCR) described in U.S. Pat. Nos. 4,683,202 and 4,683,195.

Any specimen nucleic acid, in purified or nonpurified form, can be utilized as the starting nucleic acid or acids, provided it contains, or is suspected of containing, the specific nucleic acid sequence containing the target nucleic acid. Thus, the process may employ, for example, DNA or RNA, which may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The nucleotide sequence to be amplified, may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA, as long as the mitochondrial DNA is included.

Where the target nucleotide sequence of the sample contains two strands, it is necessary to separate the strands of the nucleic acid before it can be used as the template. Strand separation can be effected either as a separate step or simultaneously with the synthesis of the primer extension products. This strand separation can be accomplished using various suitable denaturing conditions, including physical, chemical, or enzymatic means; the word "denaturing" includes all such means. One physical method of separating nucleic acid strands involves heating the nucleic acid until it is denatured. Typical heat denaturation may involve temperatures ranging from about 80° to 105° C. for times ranging from about 1 to 10 minutes. Strand separation may also be induced by an enzyme from the class of enzymes known as helicases or by the enzyme RecA, which has helicase activity, and in the presence of riboATP, is known to denature DNA. The reaction conditions suitable for strand separation of nucleic acids with helicases are described by Kuhn Hoffmann-Berling (*CSH-Quantitative Biology*, 43:63, 1978) and techniques for using RecA are reviewed in C. Radding (*Ann. Rev. Genetics*, 16:405–437, 1982).

Once the nucleic acid containing the target nucleic acid to be amplified is single stranded, the complement of each strand is synthesized by adding specific complementary oligonucleotide primers. The primer extension products are synthesized in the presence of primer, an agent for polymerization, and the four deoxynucleoside triphosphates described below. The product will be complementary to the single-stranded nucleic acid and will hybridize with a single-stranded target sequence.

When complementary strands of nucleic acid or acids are separated, regardless of whether the nucleic acid was originally double or single stranded, the separated strands are ready to be used as a template for the synthesis of additional nucleic acid strands. This synthesis is performed under conditions allowing hybridization of primers to templates to occur. Generally synthesis occurs in a buffered aqueous solution, preferably at a pH of 7–9, most preferably about 8. Preferably, a molar excess (for genomic nucleic acid, usually about $10^8$:1 primer:template) of the two oligonucleotide primers is added to the buffer containing the separated template strands. It is understood, however, that the amount of complementary strand may not be known if the process of the invention is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complex long-chain nucleic acid strands. A large molar excess is preferred to improve the efficiency of the process.

In some amplification embodiments, the substrates, for example, the deoxyribonucleotide triphosphates dATP, dCTP, dGTP, and dTTP, are added to the synthesis mixture, either separately or together with the primers, in adequate amounts and the resulting solution is heated to about 90°–100° C. from about 1 to 10 minutes, preferably from 1 to 4 minutes. After this heating period, the solution is allowed to cool to a temperature, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C. Most conveniently the reaction occurs at room temperature.

The agent for polymerization may be any compound or system which will function to accomplish the synthesis of primer extension products, including enzymes. Suitable enzymes for this purpose include, for example, *E. coli* DNA polymerase I, Taq DNA polymerase, Klenow fragment of *E. coli* DNA polymerase I, T4 DNA polymerase, other available DNA polymerases, polymerase muteins, reverse transcriptase, ligase, and other enzymes, including heat-stable enzymes (i.e., those enzymes which perform primer extension after being subjected to temperatures sufficiently elevated to cause denaturation). Suitable enzymes will facilitate combination of the nucleotides in the proper manner to form the primer extension products which are complementary to each nucleotide strand. Generally, the synthesis will be initiated at the 3' end of each primer and proceed in the 5' direction along the template strand, until synthesis terminates, producing molecules of different lengths. There may be agents for polymerization, however, which initiate synthesis at the 5' end and proceed in the other direction, using the same process as described above. In any event, the method of the invention is not to be limited to the embodiments of amplification which are described herein.

The newly synthesized nucleotide strand and its complementary nucleic acid strand will form a double-stranded molecule under hybridizing conditions described above and this hybrid is used in subsequent steps of the process. In the next step, the newly synthesized double-stranded molecule is subjected to denaturing conditions using any of the procedures described above to provide single-stranded molecules.

The above process is repeated on the single-stranded molecules. Additional agent for polymerization, nucleotides, and primers may be added, if necessary, for the reaction to proceed under the conditions described above. Again, the synthesis will be initiated at one end of each of the oligonucleotide primers and will proceed along the single strands of the template to produce additional nucleic acid. After this step, half of the extension product will consist of the specific nucleic acid sequence bounded by the two primers. After subsequent steps, the extension products bound by the two primers increase exponentially.

Alteration of wild-type genes can also be detected on the basis of the alteration of a wild-type expression product of the gene. Such expression products include the mitochondrial rRNA, especially the 12S rRNA. Point mutations may be detected by amplifying and sequencing the rRNA or via molecular cloning of cDNA made from the rRNA. The sequence of the cloned cDNA can be determined using DNA sequencing techniques which are well known in the art. The cDNA can also be sequenced via the polymerase chain reaction (PCR), for example, using cycle-sequencing or asymetric PCR.

Mismatches according to the present invention can be hybridized nucleic acid duplexes which are not 100% homologous. The lack of total homology may be due to deletions, insertions, rearrangements, substitutions, or frameshift mutations. Mismatch detection can be used to detect point mutations in the gene or its rRNA product. While these techniques are less sensitive than sequencing, they are simpler to perform on a large number of samples. An example of a mismatch cleavage technique is the RNase protection method (Winter, et al., *Proc. Natl. Acad. Sci. USA*, 82:7575, 1985; Meyers, et al., *Science*, 230:1242, 1985). In the practice of the present invention, the method involves the use of a labeled riboprobe which is complementary to the human wild-type gene coding sequence. The riboprobe and either rRNA or DNA isolated from the sample are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full-length duplex RNA for the riboprobe and the rRNA or gene, but can be a segment of either. If the riboprobe comprises only a segment of the mitochondrial rRNA or gene, it may be desirable to use a number of these probes to screen the whole rRNA sequence for mismatches.

In similar fashion, DNA probes can be used to detect mismatches through enzymatic or chemical cleavage (Cotton, et al., *Proc. Natl. Acad. Sci. USA*, 85:4397, 1988; Shenk, et al., *Proc. Natl. Acad. Sci. USA*, 72:989, 1975). Alternatively, mismatches can be detected by shifts in the electrophoretic mobility of mismatched duplexes relative to matched duplexes (White, et al., *Genomics*, 12:301, 1992; Cariello, *Human Genetics*, 42:726, 1988). PCR-amplified products can be screened for alterations which cause variation in electrophoretic mobility of the single strands of DNA using SSCP analysis (Orita, et al., *Genomics*, 5:874, 1989). With either riboprobes or DNA probes, the mitochondrial rRNA or DNA which might contain a mutation can be amplified using PCR before hybridization. Changes in DNA of the mitochondrial gene can also be detected using Southern hybridization, especially if the changes are gross rearrangements, deletions, or insertions.

DNA sequences of the rRNA gene from the specimen which have been amplified by PCR may also be screened using allele-specific probes. These probes are nucleic acid oligomers, each of which contains a region of the rRNA gene sequence harboring a known mutation. For example, one oligomer may be about 15 nucleotides in length, corresponding to a portion of the rRNA gene sequence. By use of a battery of such allele-specific probes, PCR amplification products can be screened to identify the presence of a previously identified mutation in the rRNA gene. Hybridization of allele-specific probes with amplified mitochondrial rRNA sequences can be performed, for example, on a nylon filter. Hybridization to a particular probe under stringent hybridization conditions indicates the presence of the same mutation in the specimen as in the allele-specific probe.

Mutant mitochondrial rRNA genes or gene products can be detected in human body samples or specimens, such as blood. By screening such specimens, a simple early diagnosis can be achieved for susceptibility to ototoxic deafness. The diagnostic method of the present invention is useful for clinicians so that an appropriate course of treatment can be selected. For example, the mitochondrial 12S rRNA or gene displaying alteration might suggest that a particular ototoxic antibiotic be avoided in that particular patient. Other genes which might be screened for mutations causing susceptibility to ototoxic deafness may include nuclear genes encoding mitochondrial ribosomal protein genes.

The primer pairs of the present invention are useful for determination of the nucleotide sequence of the mitochondrial rRNA gene using the polymerase chain reaction. The pairs of single stranded DNA primers can be annealed to sequences within or surrounding the mitochondrial rRNA or gene in order to prime amplifying DNA synthesis of the mitochondrial rRNA or gene itself. A complete set of these primers allows synthesis of all of the nucleotides of the mitochondrial rRNA gene coding sequences. Allele-specific primers can also be used. Such primers anneal only to particular mitochondrial rRNA mutant alleles, and thus will only amplify a product in the presence of the mutant allele as a template.

In order to facilitate subsequent cloning of amplified sequences, primers may have restriction enzyme site sequences appended to their 5' ends. Thus, all nucleotides of the primers are derived from mitochondrial rRNA sequences or sequences adjacent to mitochondrial rRNA except the few nucleotides necessary to form a restriction enzyme site. Such enzymes and sites are well known in the art. The primers themselves can be synthesized using techniques which are well known in the art. Generally, the primers can be made using synthesizing machines which are commercially available. Given that the sequence of the mitochondrial rRNA is known (Anderson, et al., *Nature*, 290:457, 1981) design of particular primers is well within the skill of the art.

The nucleic acid probes provided by the present invention are useful for a number of purposes. They can be used in Southern hybridization to genomic DNA and in the RNase protection method for detecting point mutations already discussed above. The probes can be used to detect amplification products. They may also be used to detect mismatches with the mitochondrial rRNA gene or rRNA using other techniques. Mismatches can be detected using either enzymes (e.g., S1 nuclease), chemicals (e.g., hydroxylamine or osmium tetroxide and piperidine), or changes in electrophoretic mobility of mismatched hybrids as compared to totally matched hybrids or of single strands of the target sequence. These techniques are known in the art, (Cotton, supra; Shenk, supra; Myers, supra; Winter, supra; White, supra; Orita, supra; and Novack, et al., *Proc. Natl. Acad. Sci. USA*, 83:586, 1986). Generally, the probes are complementary to mitochondrial rRNA gene coding sequences, although probes to the corresponding region of the rRNA are also contemplated. An entire battery of nucleic acid probes is used to compose a kit for detecting alteration of wild-type mitochondrial rRNA genes. The kit allows for hybridization to the entire mitochondrial rRNA gene. The probes may overlap with each other or be contiguous. In one preferred embodiment where the mutation for enhanced susceptibility to ototoxin is at nucleotide 1555 of the mitochondrial 12S rRNA, a hybridization probe is utilized which is capable of hybridizing with mitochondrial nucleotide sequences comprising 5'-CGA●CTT●GTC●TCC●TCT-3' (SEQ. I.D. NO.1), for normal sequence, 5'-CGA●CTT●GCC●TCC●TCT-3' (SEQ. I.D. NO.2), for mutant sequence, and sequences complementary thereto.

If a riboprobe is used to detect mismatches with rRNA, it is complementary to the rRNA of the human wild-type mitochondrial rRNA gene. The riboprobe generally will be labeled with radioactive, colorimetric, or fluorometric materials, which can be accomplished by any means known in the art. If the riboprobe is used to detect mismatches with DNA, it can be of either sense or antisense polarity. Similarly, DNA probes also may be used to detect mismatches.

Nucleic acid probes may also be complementary to mutant alleles of the mitochondrial 12S rRNA gene. These are useful to detect similar mutations in other patients on the basis of hybridization rather than mismatches. These are discussed above and referred to as allele-specific probes. As mentioned above, the mitochondrial rRNA probes can also be used in Southern hybridizations to genomic DNA to detect gross chromosomal changes such as deletions and insertions. The probes can also be used to select cDNA clones of mitochondrial rRNA genes from tissues of patients with a predisposition for ototoxic deafness as well as tissues of normal individuals with no predisposition. In addition, the probes can be used to detect mitochondrial rRNA in tissues to determine if expression is diminished as a result of alteration of wild-type mitochondrial genes. Provided with the mitochondrial rRNA coding sequence (Anderson, et al.,

*Nature*, 290:457, 1981), design of particular probes is well within the skill of the ordinary artisan.

In an embodiment of the invention, purified nucleic acid fragments containing oligonucleotide sequences of 10–50 bases are radioactively labelled. The labelled preparations are used to probe nucleic acid by the Southern hybridization technique Nucleotide fragments from a specimen, before or after amplification, are separated into fragments of different molecular masses by gel electrophoresis and transferred to filters which bind nucleic acid. After exposure to the labelled probe, which will hybridize to nucleotide fragments containing target nucleic acid sequences, binding of the radioactive probe to target nucleic acid fragments is identified by autoradiography (see *Genetic Engineering*, 1, ed. Robert Williamson, Academic Press, (1981), 72–81). Alternatively, nucleic acid from stool can be bound directly to filters to which the radioactive probe selectively binds nucleic acids having the specific sequences of interest and the degree of binding is quantitated by directly counting the radioactive emissions.

Where the target nucleic acid is not amplified, detection using an appropriate hybridization probe may be performed directly on the separated mammalian nucleic acid. In those instances where the target nucleic acid is amplified, detection with the appropriate hybridization probe would be performed after amplification.

The probes of the present invention can be used for examining the distribution of the specific fragments detected, as well as the quantitative (relative) degree of binding of the probe for determining the occurrence of specific strongly binding (hybridizing) sequences, thus indicating the likelihood for an individual to be at low risk or high risk for ototoxic deafness.

For the most part, the probe will be labelled with an atom or inorganic radical, most commonly using radionuclides, but also perhaps heavy metals. Conveniently, a radioactive label may be employed. Radioactive labels include $^{32}P$, $^{125}I$, $^{3}H$, $^{14}C$, $^{35}S$, or the like. Any radioactive label may be employed which provides for an adequate signal and has sufficient half-life. Other labels include ligands, which can serve as a specific binding pair member for a labelled ligand, and the like. A wide variety of labels have been employed in immunoassays which can readily be employed in the present assay. The choice of the label will be governed by the effect of the label on the rate of hybridization and binding of the probe to mutant nucleotide sequence. It will be necessary that the label provide sufficient sensitivity to detect the amount of mutant nucleotide sequence available for hybridization. Other considerations will be ease of synthesis of the probe, readily available instrumentation, ability to automate, convenience, and the like.

The manner in which the label is bound to the probe will vary depending upon the nature of the label. For a radioactive label, a wide variety of techniques can be employed. Commonly employed is nick translation with an $\alpha$-$^{32}P$-dNTP or terminal phosphate hydrolysis with alkaline phosphatase followed by labeling with radioactive $^{32}P$ employing $\gamma$-$^{32}P$-ATP and T4 polynucleotide kinase. Alternatively, nucleotides can be synthesized where one or more of the elements present are replaced with a radioactive isotope, e.g., hydrogen with tritium. If desired, complementary labelled strands can be used as probes to enhance the concentration of hybridized label.

Where other radionuclide labels are involved, various linking groups can be employed. A terminal hydroxyl can be esterified, with inorganic acids, e.g., $^{32}P$ phosphate, or $^{14}C$ organic acids, or else esterified to provide linking groups to the label. Alternatively, intermediate bases may be substituted with activatable linking groups which can then be linked to a label.

Enzymes of interest as reporter groups will primarily be alkaline phosphatase, hydrolases, particularly esterases and glycosidases, or oxidoreductases, particularly peroxidases, Fluorescent compounds include fluorescein and its derivatives, rhodamine and its derivatives, dansyl, umbelliferone, and so forth. Chemiluminescers include, for example, luciferin, and 2,3-dihydrophthalazinediones (e.g., luminol).

The probe can be employed for hybridizing to a nucleotide sequence affixed to a water insoluble porous support. Depending upon the source of the nucleic acid, the manner in which the nucleic acid is affixed to the support may vary. Those of ordinary skill in the art know, or can easily ascertain, different supports which can be used in the method of the invention.

The nucleic acid from a specimen is spotted or spread onto a filter to provide a plurality of individual portions. The filter is an inert porous solid support, e.g., nitrocellulose or nylon membranes. Any mammalian cells present in the specimen are treated to liberate their nucleic acid. The lysing and denaturation of nucleic acid, as well as the subsequent washings, can be achieved with an appropriate solution for a sufficient time to lyse the cells and denature the nucleic acid. Other denaturation agents include elevated temperatures, organic reagents (e.g., alcohols, amides, amines, ureas, phenols and sulfoxides) or certain inorganic ions (e.g., thiocyanate and perchlorate). Alternatively, nucleic acid can be isolated from blood using standard procedures with the DNA subsequently applied to the membrane.

After denaturation, the filter is washed in an aqueous buffered solution, such as Tris, generally at a pH of about 6 to 8, usually 7. One or more washings may be involved, conveniently using the same procedure as employed for the lysing and denaturation. After the lysing, denaturing, and washes have been accomplished, the nucleic acid spotted filter is dried at an elevated temperature, generally from about 50° C. to 70° C. or UV-crosslinked (for nylon membranes). Under this procedure, the nucleic acid is fixed in position and can be assayed with the probe when convenient.

Pre-hybridization may be accomplished by incubating the filter at a mildly elevated temperature for a sufficient time with the hybridization solution without the probe to thoroughly wet the filter. Various hybridization solutions may be employed, comprising from about 20% to 60% volume, preferably 30%, of an inert polar organic solvent or aqueous hybridization solutions.

The particular hybridization technique is not essential to the invention. Other hybridization techniques are well known or easily ascertained by one of ordinary skill in the art. As improvements are made in hybridization techniques they can readily be applied in the method of the invention.

The amount of labelled probe which is present in the hybridization solution will vary widely, depending upon the nature of the label, the amount of the labelled probe which can reasonably bind to the filter, and the stringency of the hybridization. Generally, substantial excess over stoichiometric concentrations of the probe will be employed to enhance the rate of binding of the probe to the fixed target nucleic acid.

Various degrees of stringency of hybridization may be employed. The more stringent the conditions, the greater the complementarity that is required for hybridization between the probe and the single stranded target nucleic acid sequence for duplex formation. Stringency can be controlled by temperature, probe concentration, probe length, ionic strength, time, and the like. Conveniently, the stringency of hybridization is varied by changing the polarity of the reactant solution by manipulating the concentration of formamide in the range of 20% to 50%. Temperatures employed will normally be in the range of about 20° C. to 80° C., usually 30° C. to 75° C. (see, generally, *Current Protocols in Molecular Biology*, Ausubel, ed., Wiley & Sons, 1989). Alternatively, stringency can be controlled when the non-annealed probe is washed off.

After the filter has been contacted with a hybridization solution at a moderate temperature for a period of time sufficient to allow hybridization to occur, the filter is then introduced into a second solution having sodium chloride, sodium citrate and sodium dodecylsulfate. The time for which the filter is maintained in the second solution may vary from five minutes to three hours or more. The second solution and the temperature (generally 5° C. below the melting temperature) determines the stringency, dissolving duplexes, and short complementary sequences. For short oligonucloetide probes, the melting temperature can be standarized according to probe length, rather than sequence, by including tetramethyl ammonium chloride in the wash solution (DiLella and Woo, *Meth. Enzymol.*, 152:447, 1987). The filter may now be assayed for the presence of duplexes in accordance with the nature of the label. Where the label is radioactive, the filter is dried and exposed to X-ray film. The materials for use in the assay of the invention are ideally suited for the preparation of a kit. Such a kit may comprise a carrier means being compartmentalized to receive in close confinement one or more container means such as vials, tubes, and the like, each of the container means comprising one of the separate elements to be used in the method.

For example, one of the container means may comprise a hybridization probe which is or can be detectably labelled. If present, a second container may comprise a lysis buffer. The kit may also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radionuclide label.

According to the present invention, a method is also provided of supplying wild-type mitochondrial rRNA function to a cell which carries mutant mitochondrial rRNA alleles. Supplying such function should suppress predisposition to ototoxic deafness. The wild-type mitochondrial rRNA gene or a part of the gene may be introduced into the cell in a vector such that the gene remains extrachromosomal. In such a situation, the gene will be expressed by the cell from the extrachromosomal location. If a gene portion is introduced and expressed in a cell carrying a mutant mitochondrial rRNA allele, the gene portion should encode a part of the mitochondrial rRNA which is required for non-susceptibility to ototoxic deafness. More preferred is the situation where the wild-type mitochondrial rRNA gene or a part of it is introduced into the mutant cell in such a way that it recombines with the endogenous mutant mitochondrial rRNA gene present in the mitochondria. Methods for introducing DNA into cells such as electroporation, calcium phosphate co-precipitation and viral transduction are known in the art and the choice of method is within the competence of the routineer. Cells transformed with the wild-type mitochondrial rRNA gene can be used as model systems to study loss of susceptibility to ototoxic deafness and drug treatments which do not induce ototoxic deafness in susceptible individuals.

Predisposition to ototoxic deafness can be ascertained by testing normal tissues of humans for mutations of mitochondrial rRNA gene. For example, a person who has inherited a germline mitochondrial rRNA mutation might be prone to ototoxic deafness. This can be determined by testing DNA encoding mitochondrial rRNA from any tissue of the person's body. Most simply, blood can be drawn and DNA encoding mitochondrial rRNA extracted from the cells of the blood. In addition, prenatal diagnosis can be accomplished by testing fetal cells or amniotic fluid for appropriate susceptibility mutations of the mitochondrial rRNA gene. Alteration of a wild-type mitochondrial rRNA allele, whether, for example, by point mutation or by deletion, can be detected by any of the means discussed above.

Molecules of cDNA according to the present invention are intron-free, mitochondrial rRNA gene coding molecules. They can be made by reverse transcriptase using the mitochondrial rRNA as a template. These molecules can be propagated in vectors and cell lines as is known in the art. The cDNA can also be made using the techniques of synthetic chemistry.

The above disclosure generally describes the present invention. A more complete understanding can be obtained by reference to the following specific examples which are provided herein for purposes of illustration only and are not intended to limit the scope of the invention.

EXAMPLE 1

Detection of Familial Deafness Mutation

Figure 1A:
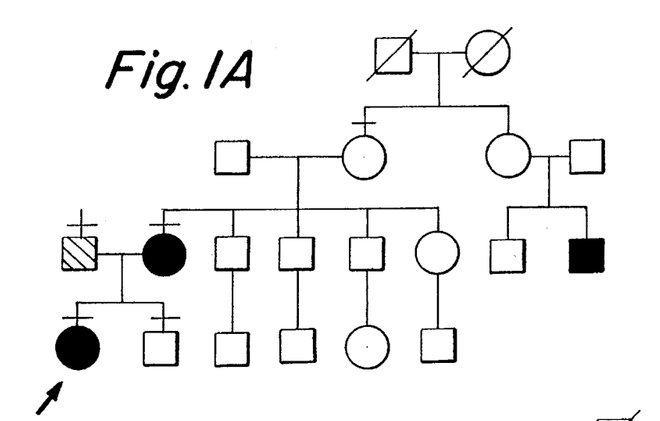
Figure 1B:
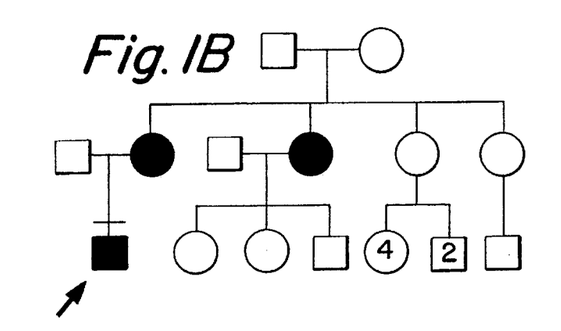
Figure 1C:
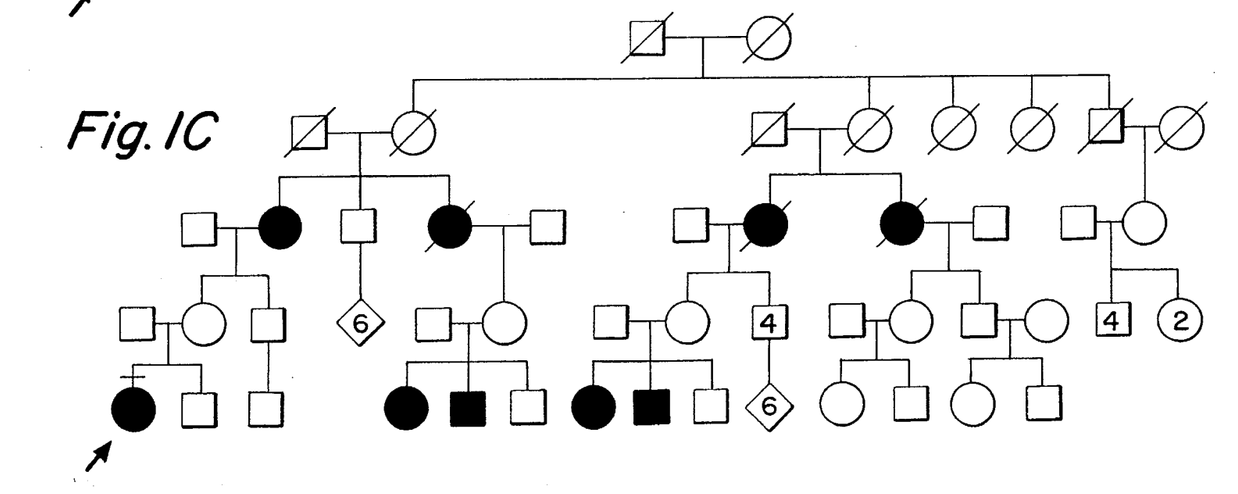

This example describes the genetic analysis of three pedigrees with maternally-transmitted aminoglycoside-induced deafness (FIG. 1). All the affected individuals developed high frequency sensorineural hearing loss after receiving streptomycin.

In this study, PCR-amplified products encompassing the mitochondrial 12S and 16S rRNA genes, between nucleotides (nt) 648–1601 and 1671–3229, respectively, were directly sequenced (Anderson, et al., *Nature*, 290:457–465, 1981). Sequences were obtained from two independent patients, the proband's mother from pedigree A and the proband from pedigree C in FIG. 1. Both patients have the same four sequence changes in the 12S rRNA gene: 663 A→G, 750 A→G, 1438 A→G, 1555 A→G, and three sequence changes in the 16S rRNA gene: 1736 A→G, 2706 A→G, and a 1 base deletion at nucleotide 3107. The "mutations" at nt 750, 1438, 2706, and 3107 are actually errors in the Cambridge sequence (Marzuki, et al., *Hum. Genet.*, 88:139–145, 1991). Allele-specific oligonucleotide hybridization (Conner, et al., *Proc. Natl. Acad. Sci. USA*, 80:278–282, 1983; Saiki, et al., *Nature*, 324:163–166, 1986; DiLella, et al., *Meth. Enzymol.*, 152:447–451, 1987) was used to screen another patient with ototoxic deafness (proband B in FIG. 1), as well as hearing controls, for the three "real" mutations 663 A→G, 1555 A→G, and 1736 A→G. All three mutations were also present in the third patient.

The mutation 1555 A→G in the 12S rRNA gene has not been found in 278 controls, including 138 Asians (117 Chinese, 21 non-Chinese), 60 Arabs, 55 Caucasians, and 25 Blacks, while both the 663 A→G and 1736 A→G mutations occurred in 11% (13 of 115) and 10% (13 of 130) of Asian controls. The same 13 controls have both the 663 and 1736 mutations. The 1555 A→G mutation is homoplasmic in these three pedigrees (see below).

A. DNA PROCESSING AND AMPLIFICATION

DNA was isolated from blood samples, except for proband C, the cousin of the Arab-Israeli proband, and 33 controls. In these latter cases, the DNA was isolated from EBV-transformed lymphoblastoid cell lines. A total of 278 controls were tested which included 138 Asians (117 Chinese, 21 non-Chinese), 60 Arab-Israelis, 55 Caucasians, and 25 Blacks.

mtDNA was amplified (Saiki, et al., *Science*, 239:487–491, 1988) using 100 ng DNA, 10 pmol of each primer, 10 mM Tris-HCl, pH 8.3, 50 mM KCl, 1.5 mM $MgCl_2$, 200 µM dNTPs and 1 U Taq DNA polymerase (Perkin-Elmer/Cetus) in a volume of 25–100 µl, with an initial 5 min denaturation at 95° C., 30 sec; 55° C., 1 min; 65° C., 1.5 min/kb in a Perkin-Elmer/Cetus thermal cycler.

In order to sequence by PCR, the PCR products were purified from low-melting point agarose gels (GeneLine LMP agarose, Beckman Instruments), with Promega's Magic Prep™ kit, and sequenced with the New England Biolabs cycle-sequencing kit, using [$\alpha$-$^{35}$S]dATP (NEN/Dupont).

B. MUTATIONAL ANALYSIS

Allele-specific oligonucleotide hybridizations (Conner, et al., *Proc. Natl. Acad. Sci. USA*, 80:278–282, 1983; Saiki, et al., *Nature*, 324:163–166, 1986) were carried out on PCR products which were boiled, diluted in chilled 18×SSC, and spotted onto magnaNT nylon filters (Micron Separations, Inc.) with a dot-blot manifold (Schleicher and Schuell). Synthetic 15-mer oligonucleotides (Oligos, Etc., Inc.), with the mutant or normal nucleotide in the central position, as described above, were 3' end-labelled with [$\alpha$-$^{32}$P]dCTP (ICN Biomedicals), or the digoxigenin-ddUTP supplied in the 3' end-labelling kit of Boehringer Mannheim Biochemicals. Hybridizations were at 37° C., in the buffer recommended, in a hybridization incubator (Robbins Scientific). After initial washes in 2×SSC, 0.1% SDS, at room temperature, the stringent wash contained 3M tetramethyl ammonium chloride (Sigma Chemical Co.), 50 mM Tris-HCl, pH 8.0, 2 mM EDTA, at 46° C. (DiLella, et al., *Meth. Enzymol.*, 152:447–451, 1987). For digoxigenin-labelled probes, the labelled moiety was detected chemiluminescently, according to the manufacturer.

For mutations which altered restriction sites, PCR products were synthesized which included an additional site for the enzyme being tested, as a positive control for complete digestion and heteroplasmy. Reaction products were digested according to manufacturer's instructions (New England Biolabs), with PCR products used directly or first isolated in low-melting point agarose with 50 mM Tris-acetate, pH 8.2 buffer. Restriction digests were electrophoresed and visualized by staining with ethidium bromide.

Trapped-oligonucleotide nucleotide incorporation (TONI) assays were performed as described (Prezant, et al., *Hum. Mut.*, 1:159–164, 1992). Briefly, a 5' biotinylated oligonucleotide, with its 3' end adjacent to the mutation site, was elongated by incorporation of the template-specified next nucleotide. Parallel reactions included only one radioactive [$\alpha$-$^{32}$P]dNTP, corresponding to the normal or mutant sequence. The radiolabelled oligonucleotide reaction products were trapped by streptavidin-linked magnetic beads (Advanced Magnetics), washed, and quantitated by Cerenkov counts in a liquid scintillation counter.

For Southern blot analyses, 1 µg genomic blood DNA was digested with 8 U BsmAI (New England Biolabs). After electrophoresis through 1.5% agarose and capillary transfer to a nylon membrane (MagnaNT, Micron Separations, Inc.), the blot was hybridized with an [$\alpha$-$^{32}$P]dCTP-labelled (ICN Biomedicals) mtDNA fragment (a PCR product between nt 319 and 2590), labelled with Amersham's multiprime kit, in Boehringer Mannheim's hybridization buffer, at 55° C. for 16 hr. The stringent wash contained 0.1×SSC, 0.1% SDS, at 55° C.

Sequence analysis of the rRNA genes in an Arab-Israeli pedigree with congenital maternally inherited deafness resulted in the identification of 9 mutations in the 12S rRNA gene and 3 in the 16S rRNA gene, including the four errors in the Cambridge sequence mentioned above. Of the seven "real" mutations in the 12S rRNA gene, four were rarely or never seen in controls (825 T→A, 851 A→G, 930 G→A, and 1555 A→G); the single mutation in the 16S rRNA gene (1822 T→C) is also very rare. Except for the 1555 A→G mutation, these residues are not evolutionarily conserved (Neefs, et al., *Nucl. Acids Res.*, 19 Supplement: 1987–2018, 1991; Gutell, et al., *Prog. in Nucl. Acid Res. & Molec. Biol.*, 32:155–216, 1985; Gutell, et al., *Nucl. Acids Res.*, 26:167–180, 1981).

All of the mtDNA mutations appeared homoplasmic upon sequencing both strands of DNA fragments amplified by PCR, and by SSCP/heteroduplex analysis. In addition, the analytic methods used to test for the mutations in at least 12–20 family members would have detected heteroplasmy if the normal sequence were present at levels of 10% or more. All restriction digests were complete, because the PCR products were chosen to include a control site for each enzyme. Also, no evidence of heteroplasmy was found in the allele-specific oligonucleotide hybridizations (Conner, supra; Saiki, supra; DiLella, supra).

The possibility of heteroplasmy for the 1555 A→G mutation, which abolishes a BsmAI restriction site, was investigated by performing Southern blot analysis. The normal mtDNA has two BsmAI fragments of 1106 and 1460 bp in this region, while patients have the corresponding mutant fragment of 2566 bp. Genomic DNA digests from three members of the Arab-Israeli pedigree (two deaf and one unaffected), five members of the pedigrees with ototoxic deafness (4 from Family A and the proband from Family B), and a hearing control were compared and no evidence of heteroplasmy was found, since the deaf pedigree members had no normal sized BsmAI fragments.

The rare mutations from the Arab-Israeli pedigree, highlighted in bold in Table 1, were screened in the three pedigrees with ototoxic deafness. None of these rare mutations was found in any of them, except for the 1555 A→G mutation which was present in all three of the families.

TABLE 1 mtDNA MUTATIONS IN THE ARAB-ISRAELI PEDIGREE

| GENE | REPLACEMENT MUTATION | CONSERVATION* | TEST** | # OF CONTROLS WITH MUTATION/ TOTAL CONTROLS |
|---|---|---|---|---|
| 12S rRNA | 709: G→A | not cons. | ASO | 3/19 |
|  | 769: G→A | not cons. | ASO | 4/19 |
|  | 825: T→A | not cons. | ASO | 2/103 |
|  | 851: A→G | not cons. | ASO | 0/107 |
|  | 930: G→A | not cons. | ASO | 5/107 |
|  | 1018: G→A | not cons. | ASO | 4/19 |
|  | 1555: A→G | =B,M,R | ASO | 0/278 |
| 16S rRNA | 1822: T→C | not cons. | ASO | 1/110 |
| tRNA asn | 5704: C→T | =B,M,R | ASO | 0/106 |
| tRNA asp | 7521: G→A | not cons. | ASO | 3/19 |
| ATPase 6 | 8582: C→T (Ala→Val) | not cons. | Fnu4HI(−) | 1/109 |
|  | 8701: A→G (Thr→Ala) | not cons. | TONI assay | 4/16 |
|  | 8860: A→G (Thr→Ala) | not cons. | HhaI(+) | 13/17 |
| CO 3 | 9559: G→C (Arg→Pro) | not cons. | TONI assay | 5/5 |
| ND 3 | 10143: G→A (Gly→Ser) | not cons. | AluI(+) | 1/107 |
|  | 10398: A→G (Thr→Ala) | =B,M,R | ASO | 15/35 |
| ND 4 | 11025: T→C (Leu→Pro) | =B | ASO | 0/109 |
| tRNA ser (AGY) | 12236: G→A | =B,M | ASO | 6/100 |
| ND 5 | 12950: A→G (Asn→Ser) | =B,M,R,X | HhaI(+) | 0/110 |
|  | 13105: A→G (Ile→Val) | =B,M,R,X | ASO | 4/42 |
| Cyt b | 15884: G→A (Ala→Thr) | not cons. | HaeIII(−) | 3/111 |

*Conservation of amino acid for protein-coding genes, or nucleotide for rRNAs and tRNAs, in bovine (B), mouse (M), rat (R), and *Xenopus laevis* (X). Not cons. = not conserved.
**Test methods included allele-specific oligonucleotide hybridizations (ASO), RFLP analysis of PCR products, where (−) and (+) indicate loss or gain, respectively, of the restriction site indicated, and TONI assay (a template-specified nucleotide incorporation assay).
In addition to the above mutations, we found six sequence changes known to be errors in the Cambridge consensus sequence at nt 1438, 13702, 14199, 14272, 14368, and 15326 (reviewed in refs. 20 and 35) and 44 additional neutral mutations in the protein coding genes, plus three new errors in the Cambridge sequence at nt 740, 2706, and 3107 (Prezant, et al., submitted). Previously described polymorphisms include the mutations at nt 8701, 8860, 9559, and 10398 (refs. 20, 35, 43, 47). Mutations in bold occurred in <5% of controls. Controls included 35 Arab-Israelis, and Caucasians, Asians, and Blacks in equal proportions, except for the 1555 A→G mutations, which was screened in all 278 controls.

EXAMPLE 2

Detection of Sporadic Ototoxic Deafness Mutation

This example describes the results of a study of individuals with no family history of deafness, but who experienced severe hearing loss after aminoglycoside exposure.

Blood samples were obtained from 36 students (18 females, 18 males), aged 12 to 21 years, from three schools of the deaf in Beijing, and one school of the deaf in Shanghai. The age of onset of deafness ranged from under one year to 10 years, and hearing loss was diagnosed within six months of antibiotic treatment, 16 of the children had received streptomycin, 10 gentamicin, 4 kanamycin, 5 a combination of gentamicin and kanamycin, and 1 a combination of streptomycin and gentamicin. The antibiotics were given in most cases as outpatient treatment for minor febrile illnesses, such as upper respiratory infections. Severity of hearing loss as measured by audiology was severe or profound. By history, no other deaf family member, and no other family members treated with aminoglycosides without hearing loss, were known.

Patient specimens were processed as described in Example 1, except that the region of mt DNA between nucleotides 1261 and 2866 was amplified by PCR. mtDNA was amplified (Saiki, et al., Science, 239:487–491, 1988) using 100 ng DNA, 10 pmol of each primer, 10 mM Tris-HCl, pH 8.3, 50 mM KCl, 1.5 mM $MgCl_2$, 100 μM dNTPs and 1 U Taq DNA polymerase (Perkin-Elmer/Cetus) in a volume of 25 μl, with an initial 5 min denaturation at 95° C., 30 sec; 54° C., 1 min; 65° C., 3.5 min in a Perkin-Elmer/Cetus thermal cycler.

The results of this study showed the 1555 A→G mutation in the 12S ribosomal RNA gene in one of the 36 cases, using allele-specific oligonucleotide hybridization. All other 35 patients had the normal A nucleotide at this position.

Further investigation of the possibility of heteroplasmy for the 1555 A→G mutation, which abolishes a BsmAI restriction site, was done by performing Southern blot analysis. Normal mtDNA has two BsmAI sites in the region amplified between nt 1261 and 2866, resulting in restriction fragments of 206, 293, and 1106 bp, while the patients have the 206 bp fragment and the corresponding mutant fragment of 1399 bp. This Southern blot analysis showed no evidence of heteroplasmy (<<1%) in the newly identified patient with the 1555 A→G mutation. The clinical implication for the patient with the 1555 mutation is that none of his maternal relatives should use aminoglycosides.

A number of embodiments of the present invention have been described. Nevertheless, it will be understood that various modifications may be made without departing from the spirit and scope of the invention. Accordingly, it is to be understood that the invention is not to be limited by the specific illustrated embodiment, but only by the scope of the appended claims.

SUMMARY OF SEQUENCES

Sequence ID No. 1 is the nucleotide sequence of a probe which hybridizes with normal mitochondrial 12S rRNA nucleotide sequences.

Sequence ID No. 2 is the nucleotide sequence of a probe which hybridizes with mutant mitochondrial 12S rRNA nucleotide sequences.

Sequence ID No. 3 is the nucleotide sequence of the 3' end of human mitochondrial 12S rRNA.

Sequence ID No. 4 is the nucleotide sequence of the corresponding region of Sequence ID No. 3 of E. coli 16S rRNA.

---

We claim:

1. A method for screening for a genetic predisposition to ototoxic deafness in a human, comprising:
   detecting an alteration of a nucleotide 1555 of the human mitochondrial 12S rRNA gene coding sequence of FIG. 2A from an adenine to a guanine or an expression product of the altered sequence in a tissue from the human, the alteration indicating susceptibility to ototoxic deafness.

2. The method of claim 1, wherein the expression product is 12S rRNA.

3. The method of claim 2, wherein the alteration of the 12S rRNA is detected by hybridization of rRNA from the tissue to a mitochondrial rRNA gene probe.

4. The method of claim 1, wherein the alteration of the rRNA gene coding sequence is detected by hybridization of a mitochondrial rRNA gene coding sequence probe to DNA isolated from the tissue.

5. The method of claim 4, further comprising:
   subjecting mitochondrial DNA from a human not susceptible to ototoxic deafness to a Southern hybridization with the mitochondrial rRNA gene coding sequence probe; and
   comparing the hybridizations of the mitochondrial rRNA gene probe to the tissue of a human potentially susceptible to ototoxic deafness and to the tissue of the human not susceptible to ototoxic deafness.

6. The method of claim 4, wherein the mitochondrial rRNA gene coding sequence probe detects a restriction fragment length polymorphism.

7. The method of claim 1, wherein the alteration of a wild-type mitochondrial rRNA gene coding sequence is detected by identifying a mismatch between a molecule (1) and (2) wherein molecule (1) is a mitochondrial rRNA gene or mitochondrial rRNA isolated from the tissue and (2) a nucleic acid probe complementary to the human wild-type mitochondrial rRNA gene coding sequence, when molecules (1) and (2) are hybridized to each other to form a duplex.

8. The method of claim 4, wherein the mitochondrial rRNA gene coding sequence probe hybridizes to a mitochondrial rRNA nucleotide sequence selected from the group consisting of the sequence from nucleotides 648 to 1601 and portions thereof.

9. The method of claim 8, wherein the mitochondrial rRNA gene coding sequence further includes a regulatory flanking sequence.

10. The method of claim 1, wherein the alteration of the 12S rRNA gene coding sequence is detected by amplification of mitochondrial rRNA gene sequence in the tissue and hybridization of the amplified mitochondrial rRNA sequence to a nucleic acid probe which comprises a mitochondrial rRNA sequence containing a normal or mutant sequence.

11. The method of claim 1, wherein the alteration of the 12S rRNA gene coding sequence is detected by molecular cloning of the mitochondrial rRNA gene in the tissue and sequencing all or part of the cloned mitochondrial rRNA gene.

12. The method of claim 1, wherein the ototoxic deafness is caused by an aminoglycoside ototoxin.

13. The method of claim 1, wherein the alteration of the 12S rRNA gene coding sequence is detected by amplification of the mitochondrial rRNA gene in the tissue and sequencing all or part of the amplified rRNA gene.

14. The method of claim 1, wherein the alteration of the 12S rRNA gene coding sequence is detected by amplification of the mitochondrial 12S rRNA gene in the tissue, restriction enzyme digestion with BsmAI, and detection of the resulting fragments by gel electrophoresis.

15. The method of claim 1, wherein the alteration of the 12S rRNA gene coding sequence is detected by restriction enzyme digestion of the whole genomic DNA with BsmAI, and detection of the resulting fragments within the mitochondrial 12S rRNA gene by Southern blotting, including gel electrophoresis and hybridization with a labelled wild-type mitochondrial 12S rRNA sequence.

16. A nucleic acid probe complementary to an alteration of a nucleotide 1555 of the human mitochondrial 12S rRNA gene coding sequence of FIG. 2A from an adenine to a guanine or an expression product of the altered sequence, wherein the alteration is associated with ototoxic deafness.

17. A kit for detecting an alteration of a nucleotide 1555 of the human mitochondrial 12S rRNA gene having the sequence of FIG. 2A from an adenine to a guanine or an expression product of the gene, wherein the alteration is associated with susceptibility to ototoxic deafness, comprising a carrier means being compartmentalized to receive in close confinement therein one or more containers comprising a nucleic acid probe which is complementary to the alteration.

18. The kit of claim 17, wherein the kit contains a plurality of overlapping or contiguous nucleic acid probes.

19. The kit of claim 18, wherein the probes allow hybridization to the entire mitochondrial 12S rRNA gene.

* * * * *